United States Patent
Elmaghraby et al.

(10) Patent No.: US 11,234,635 B2
(45) Date of Patent: Feb. 1, 2022

(54) METHOD AND SYSTEM FOR MONITORING AND EVALUATION OF PRESSURE ULCER SEVERITY

(71) Applicants: University of Louisville Research Foundation, Inc., Louisville, KY (US); Universidad de Deusto, Bilbao (ES); Fundacion Deusto, Bilbao (ES)

(72) Inventors: Adel S. Elmaghraby, Louisville, KY (US); Maria Begoña García-Zapirain Soto, Bilbao (ES); Ayman Sabry El-Baz, Louisville, KY (US)

(73) Assignees: University of Louisville Research Foundation, Inc, Louisville, KY (US); Fundacion Deusto, Bilbao (ES); Universidad de Deusto, Bilbao (ES)

( * ) Notice: Subject to any disclaimer, the term of this patent is extended or adjusted under 35 U.S.C. 154(b) by 0 days.

(21) Appl. No.: 16/614,728

(22) PCT Filed: May 18, 2018

(86) PCT No.: PCT/US2018/033468
§ 371 (c)(1),
(2) Date: Nov. 18, 2019

(87) PCT Pub. No.: WO2018/213752
PCT Pub. Date: Nov. 22, 2018

(65) Prior Publication Data
US 2021/0106274 A1    Apr. 15, 2021

Related U.S. Application Data

(60) Provisional application No. 62/508,493, filed on May 19, 2017.

(51) Int. Cl.
*A61B 5/00* (2006.01)
*G16H 30/40* (2018.01)
*G06T 7/00* (2017.01)

(52) U.S. Cl.
CPC .............. *A61B 5/445* (2013.01); *G06T 7/0016* (2013.01); *G16H 30/40* (2018.01);
(Continued)

(58) Field of Classification Search
None
See application file for complete search history.

(56) References Cited

U.S. PATENT DOCUMENTS

2004/0209237 A1    10/2004    Flewelling et al.
2010/0111386 A1    5/2010    El-Baz
(Continued)

FOREIGN PATENT DOCUMENTS

WO    WO 2016/011534 A1    1/2016
WO    WO 2018/213752 A1    11/2018

OTHER PUBLICATIONS

International Preliminary Report on Patentability (Chapter I of the Patent Cooperation Treaty) corresponding to International Patent Application No. PCT/US2018/033468 dated Nov. 28, 2019.
(Continued)

*Primary Examiner* — Vu Le
*Assistant Examiner* — Courtney Joan Nelson
(74) *Attorney, Agent, or Firm* — Jenkins, Wilson, Taylor & Hunt, P.A.

(57) ABSTRACT

Evaluating a pressure ulcer includes: detecting in a color input image a boundary of the pressure ulcer to get a RGB region of interest (ROI) image; converting the RGB ROI image to a grayscale ROI image; processing the grayscale ROI image using a Linear Combination of Discrete Gaussians (LCDG) process to estimate three main class probabili-
(Continued)

ties of the grayscale ROI image; processing the RGB ROI image using predetermined RGB values to estimate the three main class probabilities of the RGB ROI image; and combining the probabilities of the grayscale ROI image and the probabilities of the RGB ROI image to determine an estimated labeled image; and normalizing and refining the estimated labeled image using a Generalized Gauss-Markov Random Field (GGMRF) process to produce a final segmentation image.

12 Claims, 10 Drawing Sheets

(52) U.S. Cl.
CPC ............... *G06T 2207/10024* (2013.01); *G06T 2207/20076* (2013.01); *G06T 2207/20081* (2013.01); *G06T 2207/20104* (2013.01); *G06T 2207/30088* (2013.01)

(56) References Cited

U.S. PATENT DOCUMENTS

2012/0320055 A1    12/2012   Pekar et al.
2014/0228668 A1    8/2014   Wakizaka et al.

OTHER PUBLICATIONS

International Search Report and Written Opinion corresponding to International Patent Application No. PCT/US2018/033468 dated Sep. 5, 2018.
Aslan et al. (2011) A novel probabilistic simultaneous segmentation and registration using level set. 2011 18th IEEE International Conference on Image Processing, pp. 2161-2164.
Besag (1986) On the statistical analysis of dirty pictures. Journal of the Royal Statistical Society. Series B (Methodological) 48(3):259-279.
Bouman & Sauer (1993) A generalized gaussian image model for edge-preserving MAP estimation. IEEE Transactions on Image Processing 2(3):296-310.
Chan & Vese (2001) Active Contours Without Edges. IEEE Transactions on Image Processing 10(2):266-277.
Chung & Noble (1999) Statistical 3D vessel segmentation using Rician distribution. Proc Int Conf Med Image Comput Comput-Assist Intervent, pp. 82-89.
El-Baz et al. (2012) Precise segmentation of 3-D magnetic resonance angiography. IEEE Trans Biomed Eng 59(7):2019-2029.
Gimel'farb et al. (2004) Expectation-Maximization for a Linear Combination of Gaussians. Proceedings of the 17th International Conference on Pattern Recognition. ICPR 2004. vol. 3:422-425.
Kanan & Cottrell (2012) Color-to-Grayscale: Does the Method Matter in Image Recognition? PLoS ONE 7(1):e29740.
Liao et al. (2011) A generative MRF approach for automatic 3D segmentation of cerebral vasculature from 7 Tesla MRA images. Proc IEEE Int Symp Biomed Imag, pp. 2041-2044.
Tustison et al. (2010) N4ITK: improved N3 bias correction. IEEE Transactions on Medical Imaging 29(6):1310-1320.
Wilson & Noble (1999) An adaptive segmentation algorithm for time-of-flight MRA data, IEEE Trans Med Imag 18(10):938-945.

METHOD AND SYSTEM FOR MONITORING AND EVALUATION OF PRESSURE ULCER SEVERITY

RELATED APPLICATIONS

This application claims priority to U.S. Provisional Patent Application No. 62/508,493, filed May 19, 2017, the entire disclosure of which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The presently-disclosed subject matter relates to a method and system for monitoring and evaluation of pressure ulcer (bedsore) severity.

2. Description of Related Art

Patients in hospitals and long-term care facilities suffer from pressure ulcers. The cause of such ulcers is the prolonged pressure of the soft tissue between a bone prominence and an outer surface which causes localized skin injuries. Decreased blood flow due to localized pressure causes an ischemic process that takes place under the skin, making it difficult to diagnose its appearance until the wound is in an advanced state and becomes visible [1] [2]. When detection and diagnosis is delayed, health cost and deterioration of health condition occurs usually due to infection [3]. As shown in FIG. 1, various parts of the body may suffer from pressure ulcers such as the skin overlying the sacrum, coccyx, heels or the hips, but other sites such as the elbows, knees, ankles or the back of the cranium can be affected [4]. Other commonly used names are pressure sores and bed sores [5]. Preventive measures require reduction of prolonged stay without movement to reduce compression and local occlusions of blood capillaries.

Why are pressure ulcers important? In the US, the number of affected is around 2.5 million patients per year and the cost around $9.1-$11.6 billion per year. Cost of individual patient care ranges from $20,900 to $151,700 per pressure ulcer. Medicare estimated in 2007 that each pressure ulcer added $43,180 in costs to a hospital stay. More than 17,000 lawsuits are related to pressure ulcers annually. It is the second most common claim after wrongful death and greater than falls or emotional distress. Related to death, about 60,000 patients die as a direct result of a pressure ulcer each year [7]. Figures in Europe show that about the 18% of patients staying in a public or private hospital develop bedsores. The elderly are 70% of the total of patients with wounds. First weeks in hospitals are especially important because about 50% of patients develop the injuries during this time [3]. Related the death probability, the 25% of patients die because of wounds. Speaking about cost, the average treatment of bedsores in Europe ranges between 1500€ and 17000€. Some examples: the cost in Spain is around 461€ millions [9] and in the UK around 1.8 million € per year [8]. Following the classification of the National Pressure Ulcer Advisory Panel (NPUAP) [6], wounds can be associated to four different stages. In stage I, there is no loss of skin jet but the skin shows redness around the area of pressure and the affected area differs due to changes in the temperature and also the skin thickness. On stage II the bedsore has the appearance of a burn with reddish pink color and suffers of partial loss of skin thickness. On stage III the bedsore has lost full skin thickness. The stage IV is the most advanced suffering of a full skin thickness loss with exposed muscles, tendons or even bones. The patient has a higher risks of infection and the existing treatments are very painful. These visual used nowadays are invasive, painful and not as precise as required. If the patient suffers of a pressure ulcer, it is essential to proceed to make an assessment by taking into account the PUSH (Pressure Ulcer Scale for Healing) scale, which allows evaluating the evolution of the wound [12].

The clinical need addressed is related the extreme discomfort to the patient and often lead to serious, life threatening infections, which substantially increase the total cost of care. Pressure ulcers typically result from prolonged periods of uninterrupted pressure on the skin, soft tissue, muscle, and bone. Vulnerable patients include the elderly, stroke victims, patients with diabetes, those with dementia, and people who use wheelchairs or who are bedridden—any patient with impaired mobility or sensation.

Currently, nurses and medical personnel do tracking of wound/ulcer progress in a subjective manner. They may use a printed sheet to enter measurements of the wound length and width as well as their perception of tissue distribution. Standardized paper forms exist for different facilities, but there is no exact automated measurement.

BRIEF SUMMARY OF THE INVENTION

Generally described, an exemplary method for evaluating a pressure ulcer according to the invention includes: a pre-processing step of detecting in a color input image a boundary of the pressure ulcer to get a RGB region of interest (ROI) image; converting the RGB ROI image to a grayscale ROI image; processing the grayscale ROI image using a Linear Combination of Discrete Gaussians (LCDG) process to estimate three main class probabilities of the grayscale ROI image; processing the RGB ROI image using predetermined RGB values to estimate the three main class probabilities of the RGB ROI image; combining the estimated three main class probabilities of the grayscale ROI image and the estimated three main class probabilities of the RGB ROI image to determining an estimated labeled image; and normalizing and refining the estimated labeled image using a Generalized Gauss-Markov Random Field (GGMRF) process to produce a final segmentation image. Advantageously, the final segmentation allows an objective evaluation of the pressure ulcer because it provides an accurate classification of the tissue in the ulcer. The classification can then be used to objectively determine relative percentages of each of the tissue types (i.e., the tissue distribution) for evaluating the severity of the pressure ulcer.

In accordance with one implementation, processing the grayscale ROI image using a LCDG process includes: collecting a marginal empirical probability distribution $Fs = (fs(q): q \in Q)$ of gray levels; finding an initial LCDG-model that closely approximates Fs by using an initializing process to estimate numbers $C_p$-K, $C_n$, and parameters w, $\Theta$ (weights, means, and variances) of positive and negative Discrete Gaussians (DGs); refining the initial LCDG-model with the numbers $C_p$ and $C_n$ by adjusting all other parameters with an expectation-maximization (EM) method to create a final LCDG-model; splitting the final LCDG-model into K sub-models, one per each dominant mode, by minimizing expected errors of misclassification; and selecting from the K sub-models a sub-model with a largest mean value as a desired model. The steps of finding the initial LCDG-model that closely approximates Fs and refining the initial LCDG-model produce a LCDG-model with nonnegative starting probabilities $p_{w,\Theta}(q)$. The steps of splitting the final LCDG-model into K sub-models and selecting from the K sub-models a sub-model with a largest mean value increase the likelihood that the probabilities continue to be nonnegative. Thus, at the end of these steps, three probabilities for each pixel in the grayscale ROI image are obtained: $P_1$ which is the probability to be belonging to class 1, $P_2$ which is the probability to be belonging to class 2, and $P_3$ which is the probability to be belonging to class 3.

In accordance with another implementation, processing the RGB ROI image using predetermined RGB values includes: constructing a database for a set of labeled images for three main tissue classes; constructing a matrix for each class by aggregating RGB values of all pixels of that class from training images which have been labeled; for each pixel in the RGB ROI image, calculating Euclidean distances between the pixel and the matrix for each class; determining for each of the three main tissue classes a total number of voxels that are at distances lower than a predefined threshold; and estimating the three main class probabilities for each pixel in the RGB ROI image using individual probabilities.

In accordance with yet another implementation, combining the estimated three main class probabilities of the grayscale ROI image and the estimated three main class probabilities of the RGB ROI image includes: constructing the final pixel-wise probability vector as $P=P_{Gray} \times P_{Color}$; and obtaining the estimated labeled image as an initial tissue classification of each pixel using a vector element with a highest probability.

Another aspect of the invention is a method of monitoring a pressure ulcer. The method includes determining an objective change in the pressure ulcer by comparing current results of the method of evaluating the pressure ulcer described above with prior results of the method. Advantageously, the objective determinations of tissue distribution allow objective monitoring of the severity of the pressure ulcer over time.

In yet another aspect of the invention, a system for monitoring and evaluating a pressure ulcer, includes: a microprocessor; a data storage device in communication with the microprocessor; an input/output device in communication with the microprocessor; and a digital camera in communication with the microprocessor. The microprocessor is for executing instructions stored in the data storage device for: receiving a color input image of the pressure ulcer from the digital camera; detecting in the color input image a boundary of the pressure ulcer to get a RGB region of interest (ROI) image; converting the RGB ROI image to a grayscale ROI image; processing the grayscale ROI image using a Linear Combination of Discrete Gaussians (LCDG) process to estimate three main class probabilities of the grayscale ROI image; processing the RGB ROI image using predetermined RGB values to estimate the three main class probabilities of the RGB ROI image; combining the estimated three main class probabilities of the grayscale ROI image and the estimated three main class probabilities of the RGB ROI image to determining an estimated labeled image; normalizing and refining the estimated labeled image using a Generalized Gauss-Markov Random Field (GGMRF) process to produce a final segmentation image; and outputting the final segmentation image to the input/output device.

Advantageously, the instructions may be optimized for execution on a mobile device, such as a smart phone or a personal digital assistant (PDA) with respect to execution speed, memory requirements, and integration of the digital camera and power supply so that the device can be carried by a care giver and used at the patient's bedside.

In accordance with one implementation of the exemplary system, processing the grayscale ROI image using a LCDG process includes: collecting a marginal empirical probability distribution Fs=(fs(q): q∈Q) of gray levels; finding an initial LCDG-model that closely approximates Fs by using an initializing process to estimate numbers $C_p$–K, $C_n$, and parameters w, Θ (weights, means, and variances) of positive and negative Discrete Gaussians (DGs); refining the initial LCDG-model with the numbers $C_p$ and $C_n$ by adjusting all other parameters with an expectation-maximization (EM) method to create a final LCDG-model; splitting the final LCDG-model into K sub-models, one per each dominant mode, by minimizing expected errors of misclassification; and selecting from the K sub-models a sub-model with a largest mean value as a desired model. The steps of finding the initial LCDG-model that closely approximates Fs and refining the initial LCDG-model produce a LCDG-model with nonnegative starting probabilities $p_{w,\Theta}(q)$. The steps of splitting the final LCDG-model into K sub-models and selecting from the K sub-models a sub-model with a largest mean value increase the likelihood that the probabilities continue to be nonnegative. Thus, at the end of these steps, three probabilities for each pixel in the grayscale ROI image are obtained: $P_1$ which is the probability to be belonging to class 1, $P_2$ which is the probability to be belonging to class 2, and $P_3$ which is the probability to be belonging to class 3.

In accordance with another implementation of the exemplary system, processing the RGB ROI image using predetermined RGB values includes: constructing a database for a set of manually labeled images for three main tissue classes; constructing a matrix for each class by aggregating RGB values of all pixels of that class from training images which have been manually labeled by an expert; for each pixel in the RGB ROI image, calculating Euclidean distances between the pixel and the matrix for each class; determining for each of the three main tissue classes a total number of voxels that are at distances lower than a predefined threshold; and estimating the three main class probabilities for each pixel in the RGB ROI image using individual probabilities.

In accordance with yet another implementation of the exemplary system, combining the estimated three main class probabilities of the grayscale ROI image and the estimated three main class probabilities of the RGB ROI image includes: constructing the final pixel-wise probability vector as $P=P_{Gray} \times P_{Color}$; and obtaining the estimated labeled image as an initial tissue classification of each pixel using a vector element with a highest probability.

In accordance with still yet another implementation, the exemplary system includes a power supply in communication with the microprocessor, the data storage device, the input/output device, and the digital camera. The integrated power supply, the microprocessor, the data storage device, the input/output device, and the digital camera are integrated into a unitary mobile device that can be carried by a caregiver and utilized at the bedside of a patient. Advantageously, the input/output device may be a touchscreen, and the unitary mobile device may be a commercially available smart phone or personal digital assistant (PDA).

DETAIL DESCRIPTION OF EXEMPLARY EMBODIMENTS

Figure 1:
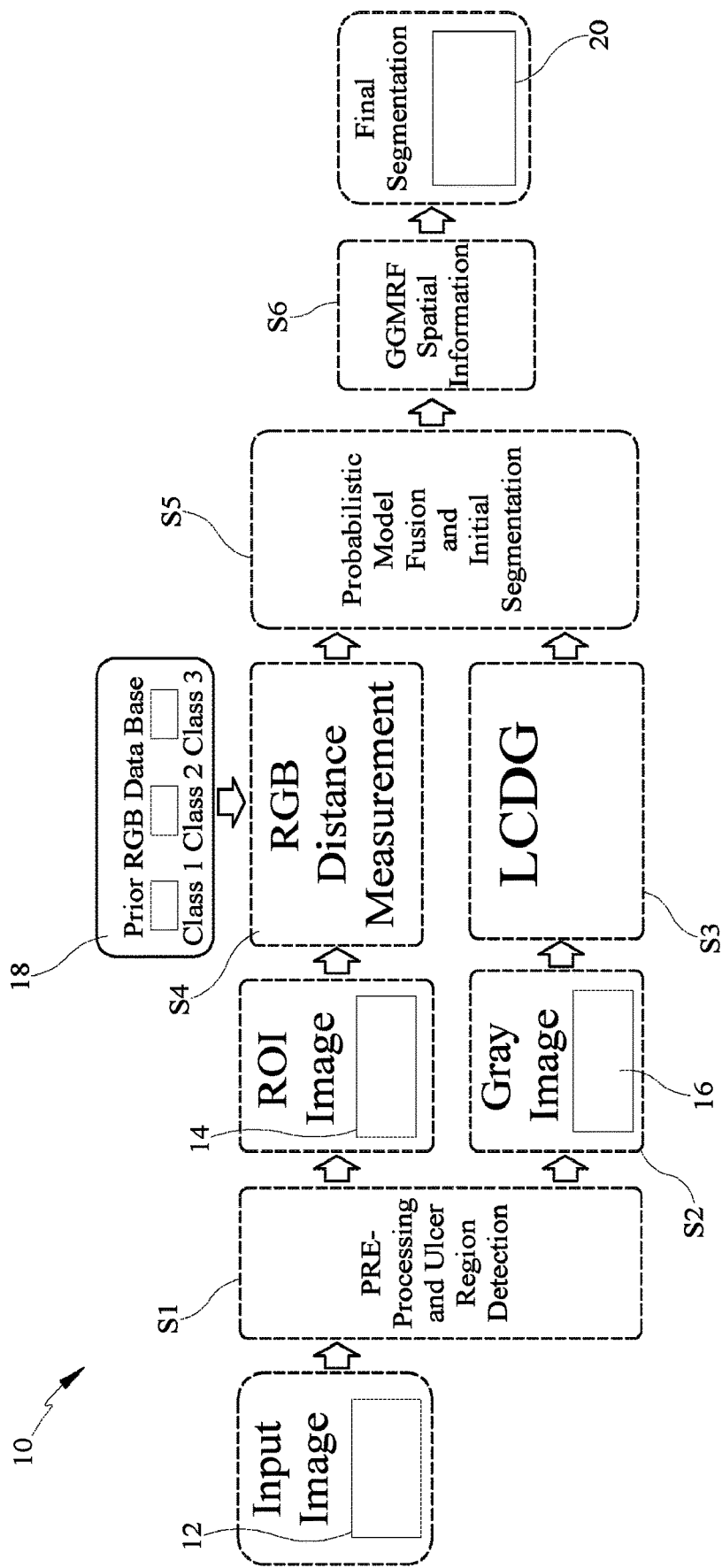
FIG. 1 is a schematic diagram of an exemplary method according to the invention.

The details of one or more embodiments of the presently-disclosed invention are set forth in this document. Modifications to embodiments described herein, and other embodiments, will be evident to those of ordinary skill in the art after a study of the information provided herein. The information provided herein, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "microprocessor" is used herein to describe one or more microprocessors, microcontrollers, central processing units, Digital Signal Processors (DSPs), Field-Programmable Gate Arrays (FPGAs), Application-Specific Integrated Circuits (ASICs), or the like for executing instructions stored on a data storage device.

As used herein, the term "data storage device" is understood to mean physical devices (computer readable media) used to store programs (sequences of instructions) or data (e.g. program state information) on a non-transient basis for use in a computer or other digital electronic device. The term "memory" is often (but not always) associated with addressable semiconductor memory, i.e. integrated circuits consisting of silicon-based transistors, used for example as primary memory but also other purposes in computers and other digital electronic devices. Semiconductor memory includes both volatile and non-volatile memory. Examples of non-volatile memory include flash memory (sometimes used as secondary, sometimes primary computer memory) and ROM/PROM/EPROM/EEPROM memory. Examples of volatile memory include dynamic RAM memory, DRAM, and static RAM memory, SRAM.

As used herein, the term "touchscreen" is used to describe an input/output device normally layered on the top of an electronic visual display of an information processing system, such that a user can give input or control the information processing system through simple or multi-touch gestures by touching the screen with a special stylus or one or more fingers.

As used herein, the term "segmentation" refers to the process of partitioning a digital image into multiple segments (sets of pixels), with a goal of simplifying or changing the representation of the image into something that is easier to analyze. More precisely, image segmentation is the process of assigning a label to every pixel in an image such that pixels with the same labels share certain characteristics.

As used herein, the term "EM algorithm" refers to, in statistics, an expectation-maximization (EM) iterative method to find maximum likelihood or maximum a posteriori (MAP) estimates of parameters in statistical models, where the model depends on unobserved latent variables. The EM iteration alternates between performing an expectation (E) step, which creates a function for the expectation of the log-likelihood evaluated using the current estimate for the parameters, and a maximization (M) step, which computes parameters maximizing the expected log-likelihood found on the E step. These parameter-estimates are then used to determine the distribution of the latent variables in the next E step.

As used herein, "Dice's coefficient" refers to a statistic used for comparing the similarity of two samples, and is also known as the "Sorensen index," the "similarity coefficient/index," or the "Dice similarity coefficient (DSC)."

An object of the invention is a commercial, low cost system and method to assess and track severity of pressure ulcers (bedsores) from digital colored images.

FIG. 1 is a schematic diagram of an exemplary method 10 according to the invention. The proposed system includes a pre-processing step, S1, of detecting in a color (RGB) input image 12 an ulcer boundary to get a RGB region of interest (ROI) image 14. The benefits of this step are to improve segmentation accuracy and minimize execution time. Another step, S2, is converting the RGB ROI image 14 to a grayscale ROI image 16. Another step, S3, is processing the grayscale ROI image 16 using a Linear Combination of Discrete Gaussians (LCDG) process [33] to calculate a marginal distribution of three main classes of gray levels. Another step, S4, is calculating, from the RGB ROI image 14, three class probabilities of using predetermined RGB values 18. Then, the next step S5, is fusing the probabilistic models calculated in steps S3 and S4 to determining an estimated labeled image (i.e., an initial segmentation). A last step S6, to preserve continuity, is normalizing and refining the estimated labeled image using a Generalized Gauss-Markov Random Field (GGMRF) process to produce a final segmentation image 20.

Advantageously, this approach provides consistency and improves tracking of patient condition allowing for better intervention if needed.

Figure 2:
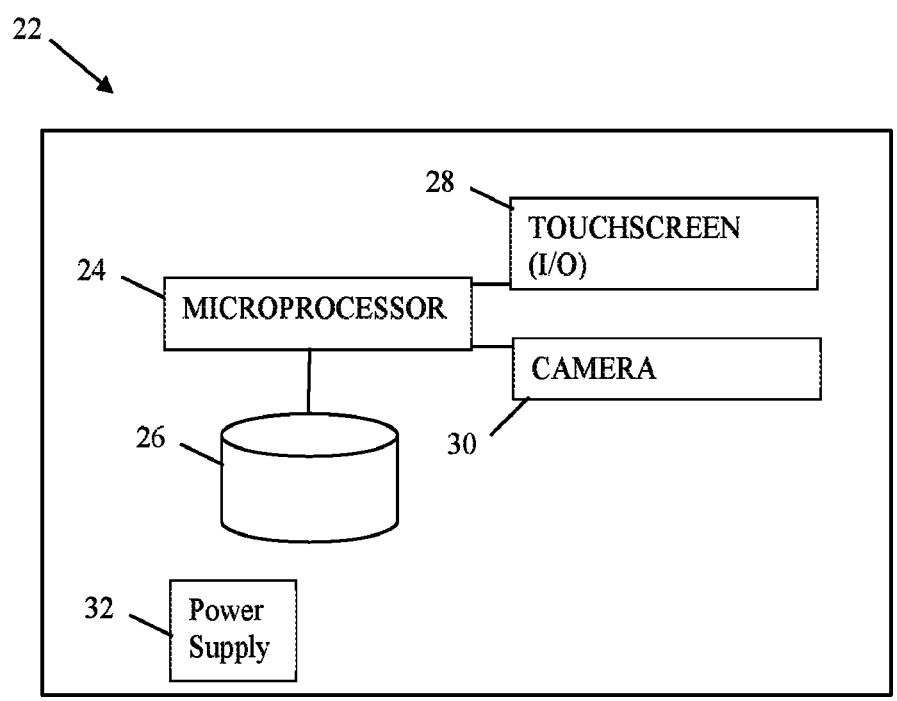
FIG. 2 is a block diagram of an exemplary system 22 according to the invention.

FIG. 2 is a block diagram of an exemplary system 22 according to the invention, including a microprocessor 24 in communication with a data storage device 26 (e.g., computer memory which may or may not be integrated with the microprocessor), an input/output device 28 (e.g., a touchscreen), and a digital camera 30. An integrated power supply 32 (i.e., a rechargeable battery) allows the exemplary system 22 to be portable. Preferably, the components are integrated into a unitary device (e.g., a smartphone or a personal digital assistant), so that the unitary device can be carried by a caregiver and utilized at the bedside of a patient. Instructions are stored in the data storage device 26 to cause the microprocessor 24 to receive and store the input image 12 (FIG. 1) from the digital camera 30, to execute the steps of the method 10 described herein, and to display the final segmentation image 20 (FIG. 1) on the input/output device 28.

A. Pre-Processing and Detection of ROI

Returning now to the exemplary method 10 describe in connection with FIG. 1, in the pre-processing step, S1, to roughly remove the unwanted parts of the input image and to detect the region of interest (ROI), i.e. ulcer region, pre-processing procedures are adopted. This step is required to crop the color (RGB) input image 12 to the RGB ROI image 14 and to minimize the execution time. Details on these procedures are discussed in the following subsections.

1. Ulcer Region Detection (ROI)

In the exemplary method 10, the pressure ulcer region in the color (RGB) input image 12 is annotated (i.e., cropped) to the ulcer boundary to get the RGB ROI image 14. For example, a commercial software called Slicer (www.slicer.org), which may be incorporated into the exemplary system 22, may be utilized. Of course, one of skill in the art will recognize that other equivalent means of cropping the input image 12 may be used without departing from the teachings of the invention.

Figure 3:
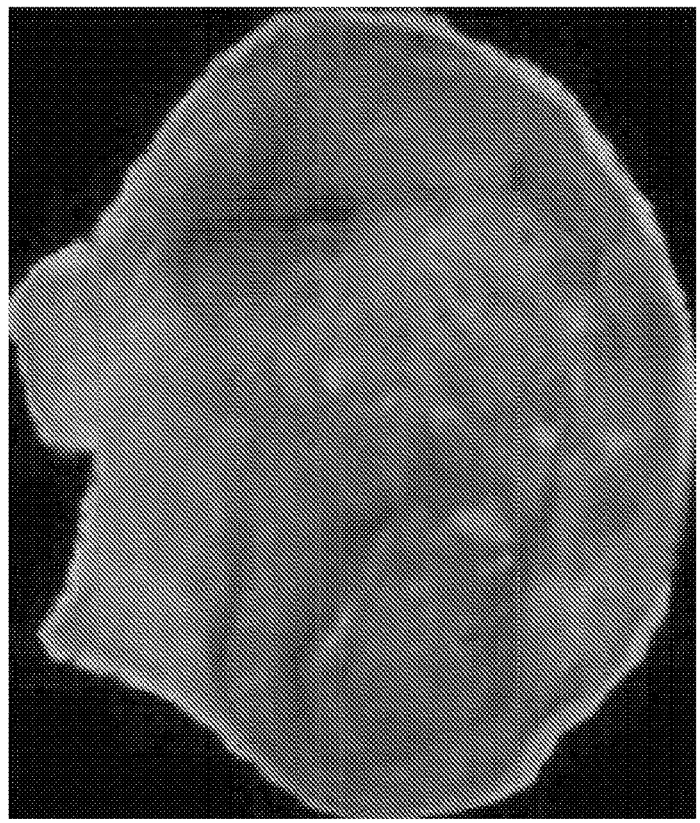
FIG. 3 and FIG. 4 are exemplary RGB ROI images of pressure ulcers.
Figure 4:
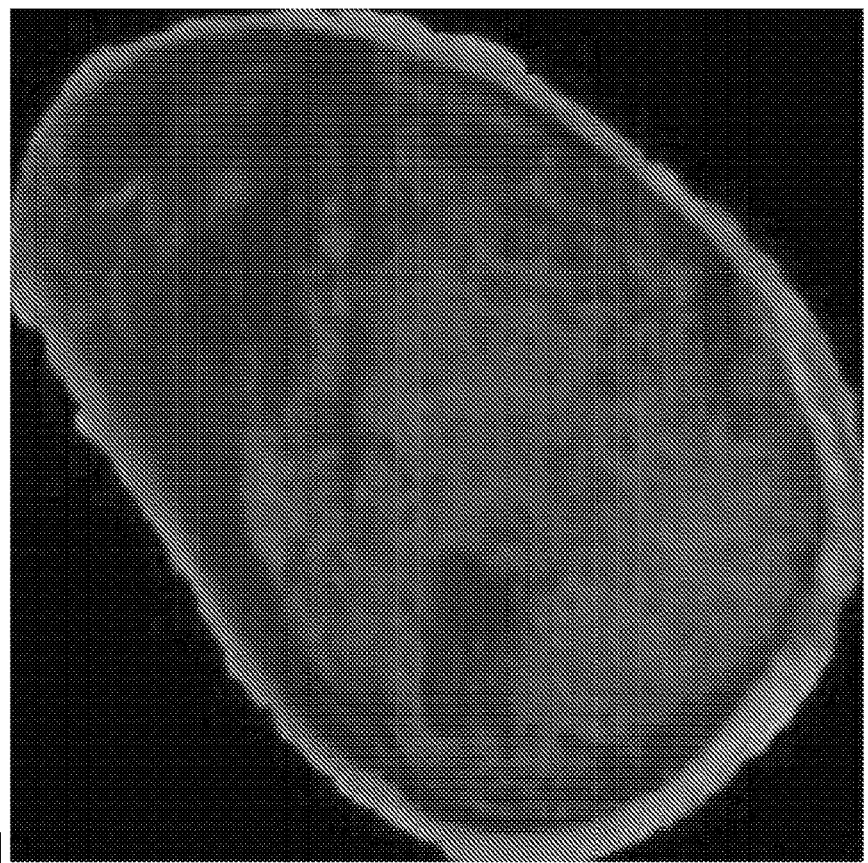

FIG. 3 and FIG. 4 are examples of cropped images of ulcer ROIs. The original size of the input images is 4000×3000 pixels. The average size of the ROI regions after cropping is 1024×1024 pixels.

2. Converting RGB to Grayscale

After the detection of ulcer region, the ROI colored image is converted to a gray image as follow:

$$G = 0.2126R + 0.7152G + 0.0722B \quad (1)$$

where, the weighting values are defined by CIE 1931 system [34]. Each pixel is captured using three values ranging from 0-255 and these are the R (red), G (green), and B (blue) values. The transformation maps each pixel into a single greyscale value ranging from 0-255 using the formula above.

The final outputs of this step are the RGB ROI image 14 and the grayscale ROI image 16 of the ulcer region. These two images 14, 16 will be used as inputs for the next steps.

B. Appearance Model Using Linear Combinations of Discrete Gaussians (LCDG)

Many important applications of image analysis deal with multimodal images such that each object of interest relates to an individual mode in the marginal signal distribution collected over the image. Segmentation of such seemingly simple images is nonetheless a challenging problem because each meaningful boundary between the objects is rarely formed by easily detectable signal differences (or "edges"). Most commonly, the signals have very close values across the boundary and relate to intersecting tails of distributions describing individual objects. To accurately segment such images, not only the main body but also the tails of each such distribution have to be precisely recovered from the available mixture. The exemplary method 10 discussed herein includes a novel process for accurate unsupervised segmentation of the grayscale ROI image 16 of the pressure ulcer. It has a considerably improved convergence to a local maximum of the image likelihood and provides a very close approximation of each distribution related to the mode with a linear combination of sign-alternate discrete Gaussian kernels. In other words, this approach is reliable and can find the optimal solution.

An expected log-likelihood is used as a model identification criterion. Let X denote the grayscale ROI image 16. Here, R and $Q = \{0, 1, \ldots, Q-1\}$ are a rectangular arithmetic lattice supporting the 2D image and a finite set of Q-ary intensities (gray levels), respectively.

Let $F_s = (f_s(q): q \in Q; \Sigma_{q \in Q} f_s(q) = 1$, where q denotes the gray level, be an empirical marginal probability distribution of gray levels for X.

In accordance with [27], each image is considered as a K-modal image with a known number K of the dominant modes related to the regions of interest (in this particular case, K=3). To segment the image by separating the modes, the individual probability distributions of the signals associated with each mode from $F_s$ are estimated. In contrast to a conventional mixture of Gaussians, one per region [25], or slightly more flexible mixtures involving other simple distributions, one per region, as e.g., in [23] and [24], $F_s$ is closely approximated with LCDG. Then, the LCDG of the image is partitioned into submodels related to each dominant mode.

The discrete Gaussian (DG) is defined as the probability distribution $\Psi_\theta = \Psi(q|\theta): q \in Q$ on Q of gray levels such that each probability $\Psi(q|\theta)$ relates to the cumulative Gaussian probability function $\Phi_\theta(q)$ as follows (here, $\theta$ is a shorthand notation $\theta = (\mu, \sigma^2)$ for the mean, $\mu$, and variance, $\sigma^2$):

$$\psi(q, \theta) \begin{cases} \phi_\theta(0.5) & \text{for } q = 0 \\ \phi_\theta(q + 0.5) - \phi_\theta(q - 0.5) & \text{for } q = 1, \ldots, Q-2 \\ 1 - \phi_\theta Q - 1.5) & \text{for } q = Q-1 \end{cases} \quad (2)$$

The LCDG with $C_p$ positive and $C_n$ negative components such that $C_p \geq K$ $$p_{w,\Theta}(q) = \sum_{r=1}^{C_p} \omega_{p,r}\psi(q|\theta_{n,l}) - \sum_{l=1}^{C_n} \omega_{n,l}\psi(q|\theta_{n,l}) \quad (3)$$

has obvious restrictions on its weights $w=[w_p, w_n]$, namely, all the weights are nonnegative and $$\sum_{r=1}^{C_p} \omega_{p,r} - \sum_{l=1}^{C_n} \omega_{n,l} = 1. \quad (4)$$

Generally, the true probabilities are nonnegative: $p_{w,\Theta}(q) \geq 0$ for all $q \in Q$. Therefore, the probability distributions comprise only a proper subset of all the LCDGs in (2), which may have negative components $p_{w,\Theta}(q) < 0$ for some $q \in Q$.

A goal of the exemplary method is to find a K-modal probability model that closely approximates the unknown marginal gray level distribution. Given $F_s$, its Bayesian estimate F is as follows [25]:

$$f(q) = (|R|f_s(q) + 1)/(|R| + Q).$$

The desired model has to maximize the expected log-likelihood of the statistically independent empirical data by the model parameters:

$$L(w,\Theta) = \Sigma_{q \in Q} f(q) \log p_{w,\Theta}(q) \quad (5)$$

For simplicity, the identification procedure is not restricted to only the true probability distributions, but instead the validity of the restrictions is checked during the procedure itself. The Bayesian probability estimate F with no zero or unit values in (5) ensures that a sufficiently large vicinity of each component f(q) complies to the restrictions. In other words, the algorithm complies with imposed constraints.

To precisely identify the LCDG-model including the numbers of its positive and negative components, Expectation Maximization (EM) based techniques [27], which allow selection based on the most likely decision, are adapted to the LCDGs for identification of a probability density with a continuous linear combination of Gaussian model.

Figure 5:
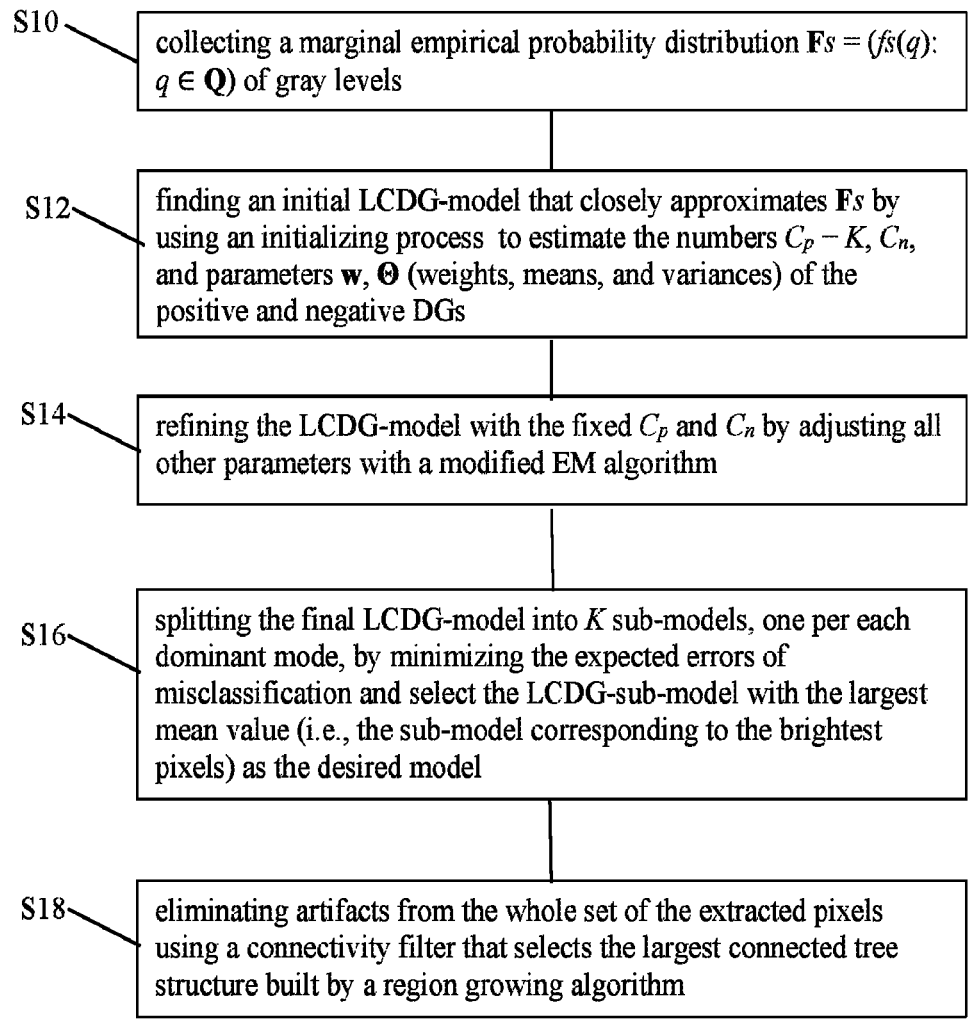
FIG. 5 is a flow chart of an exemplary Linear Combinations of Discrete Gaussians (LCDG) segmentation process.

Thus, FIG. 5 is a flow chart of an exemplary LCDG segmentation process, including the steps described below. Initially, for each image X, the steps include: S10, collecting a marginal empirical probability distribution Fs=(fs(q): q∈Q) of gray levels; S12 finding an initial LCDG-model that closely approximates Fs by using an initializing process to estimate the numbers $C_p$-K, $C_n$, and parameters w, Θ (weights, means, and variances) of the positive and negative DGs; S14 refining the LCDG-model with the fixed $C_p$ and $C_n$ by adjusting all other parameters with a modified EM algorithm; and S16, splitting the final LCDG-model into K submodels, one per each dominant mode, by minimizing the expected errors of misclassification and select the LCDG-submodel with the largest mean value (i.e., the submodel corresponding to the brightest pixels) as the desired model. Then, the next step is S18, eliminating artifacts from the whole set of the extracted pixels using a connectivity filter that selects the largest connected tree structure built by a region growing algorithm [28].

The main goal of the process is to find the threshold for each gray image that extracts the 3 classes (corresponding to the red tissues, black tissues, and yellow/white tissues) from their darker background. The initialization at S12 produces the LCDG with the nonnegative starting probabilities $p_{w,\Theta}(q)$. While the refinement at S16 increases the likelihood that the probabilities continue to be nonnegative. At the end of this step, three probabilities for each pixel in the image are obtained: $P_1$ which is the probability to be belonging to class 1 (black tissues), $P_2$ which is the probability to be belonging to class 2 (red tissues), and $P_3$ which is the probability to be belonging to class 3 (white/yellow tissues). The pixel-wise LCDG probability, $P_{Gray} = [P_1, P_2, P_3]$, is used to get the initial segmentation/labeling after the next step.

C. Prior RGB Information and Initial Segmentation

In addition to the pixel-wise LCDG probability $P_{Gray}$ estimated from the greyscale image, an additional probability, $P_{Color}$, is also estimated using prior color information and an Euclidean distance measure. Both probability vectors are then used to obtain the initial tissue segmentation. In order to estimate $P_{Color}$, a database for a set of manually labeled images for the three tissue classes 1, 2, 3 is first constructed using the color values. Namely, for each class i∈{1, 2, 3} a matrix $M_i$ is constructed by aggregating the "RGB" values of all the pixels of that class from all training images, which were manually labeled by an expert.

Figure 6:
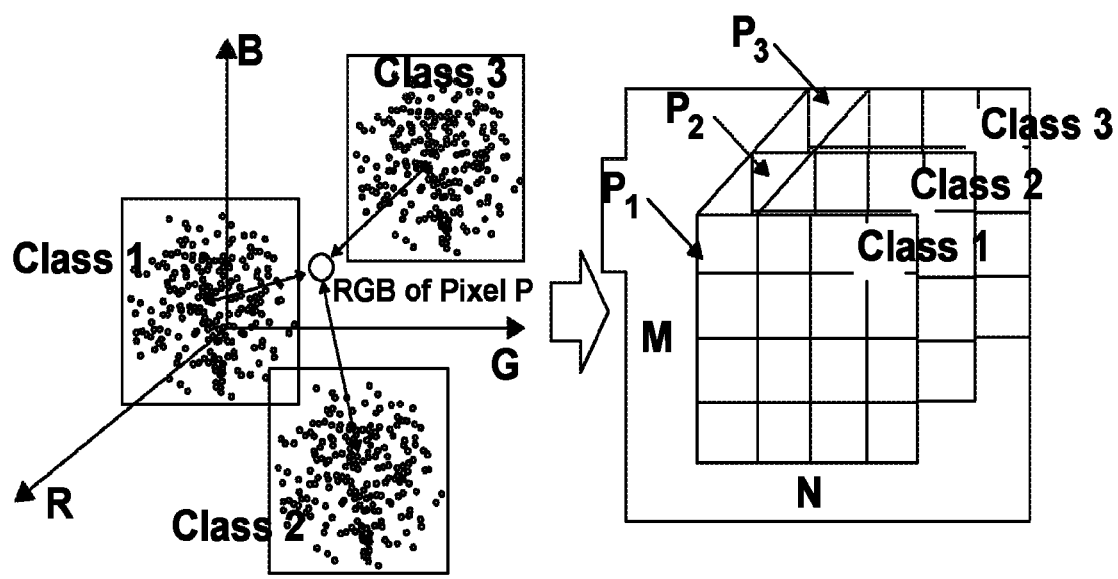
FIG. 6 is a schematic diagram of processing an exemplary pixel of a RGB ROI image for estimating the three main class probabilities of the pixel.
Figure 7:
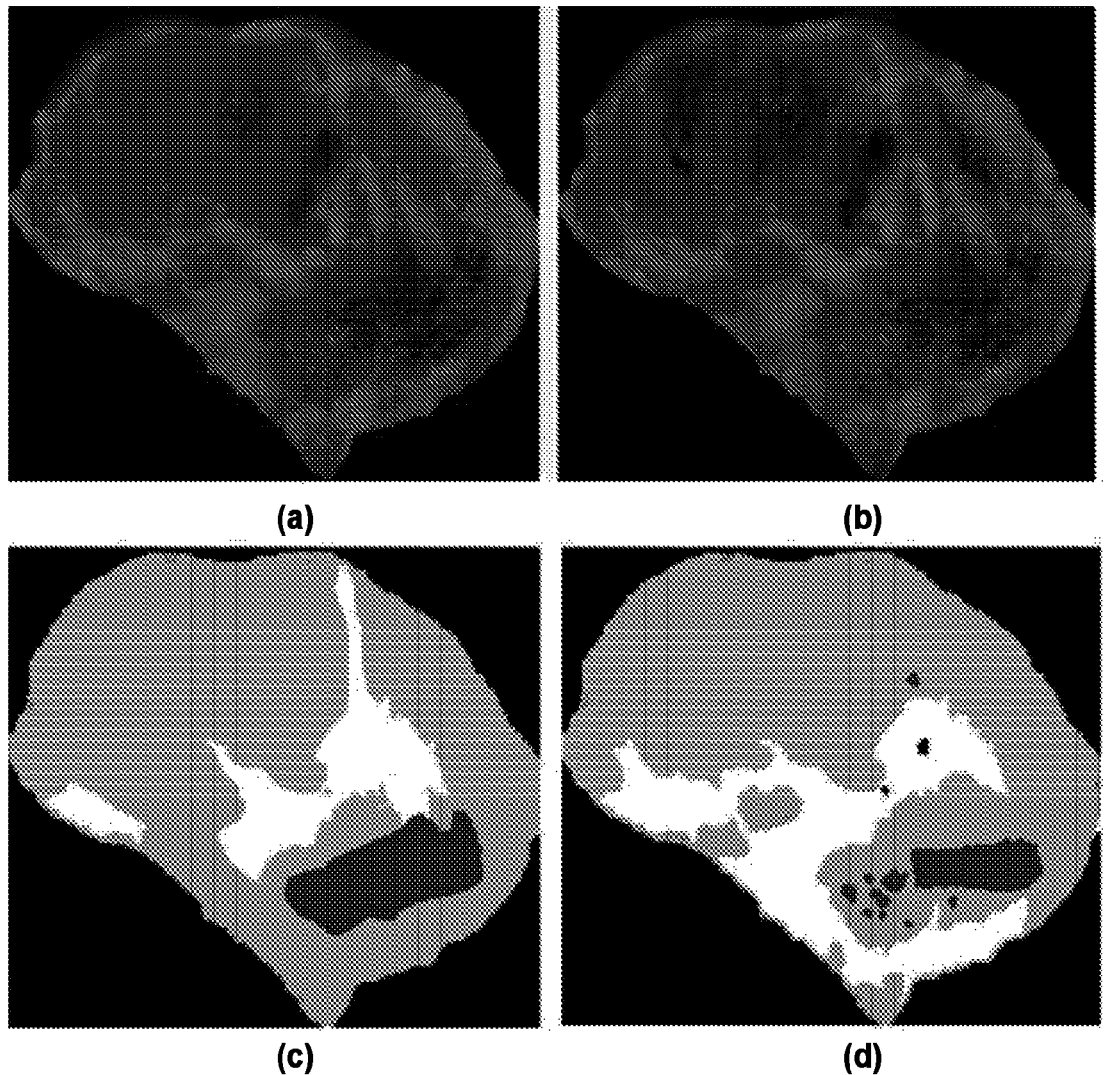
FIG. 7 through FIG. 11 are exemplary resulting images of different examples, including: (a) a colored ROI image, (b) a grayscale ROI image; (c) a segmented image resulting from the exemplary method, and (d) a resulting segmented image from a comparison method.
Figure 8:
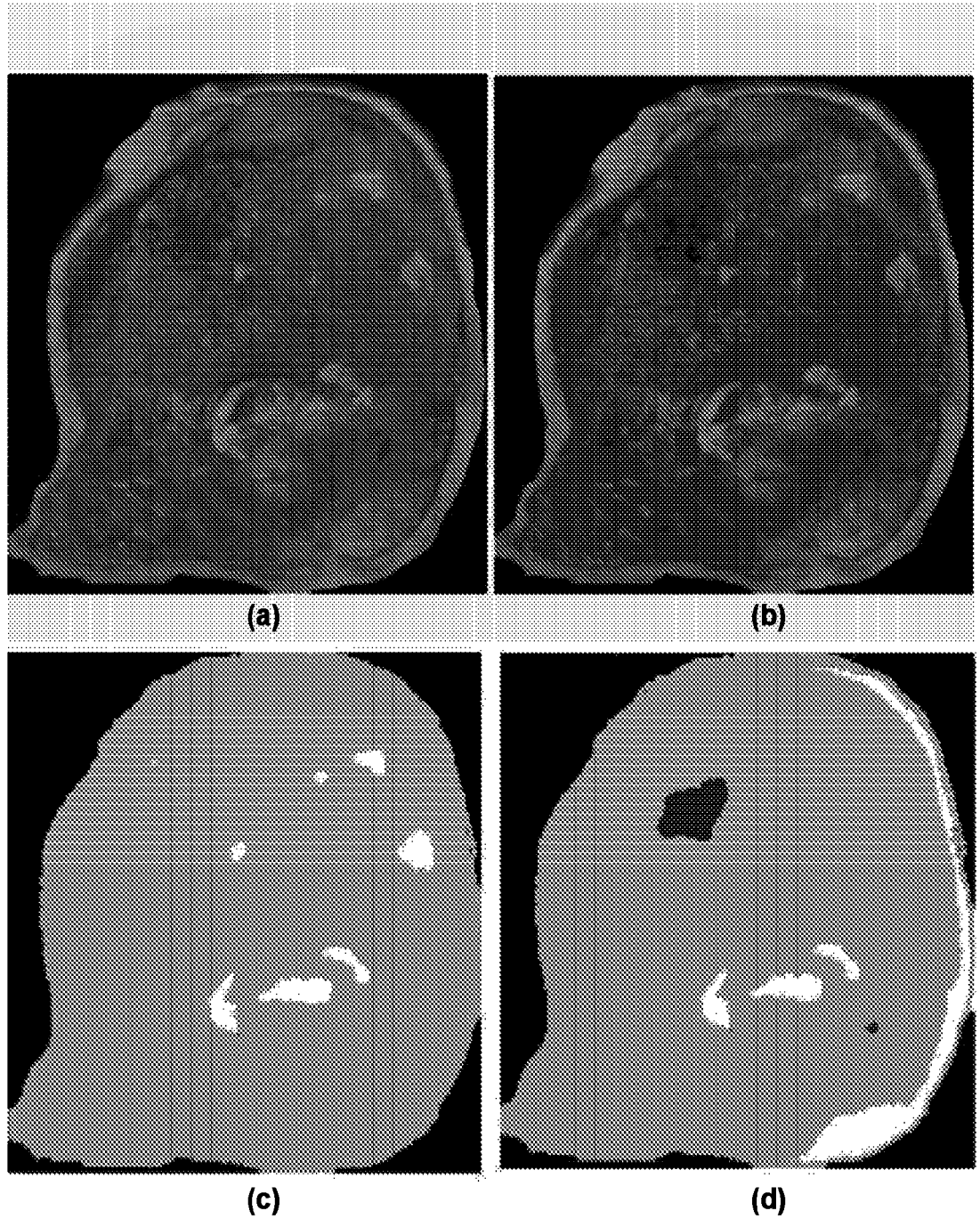
Figure 9:
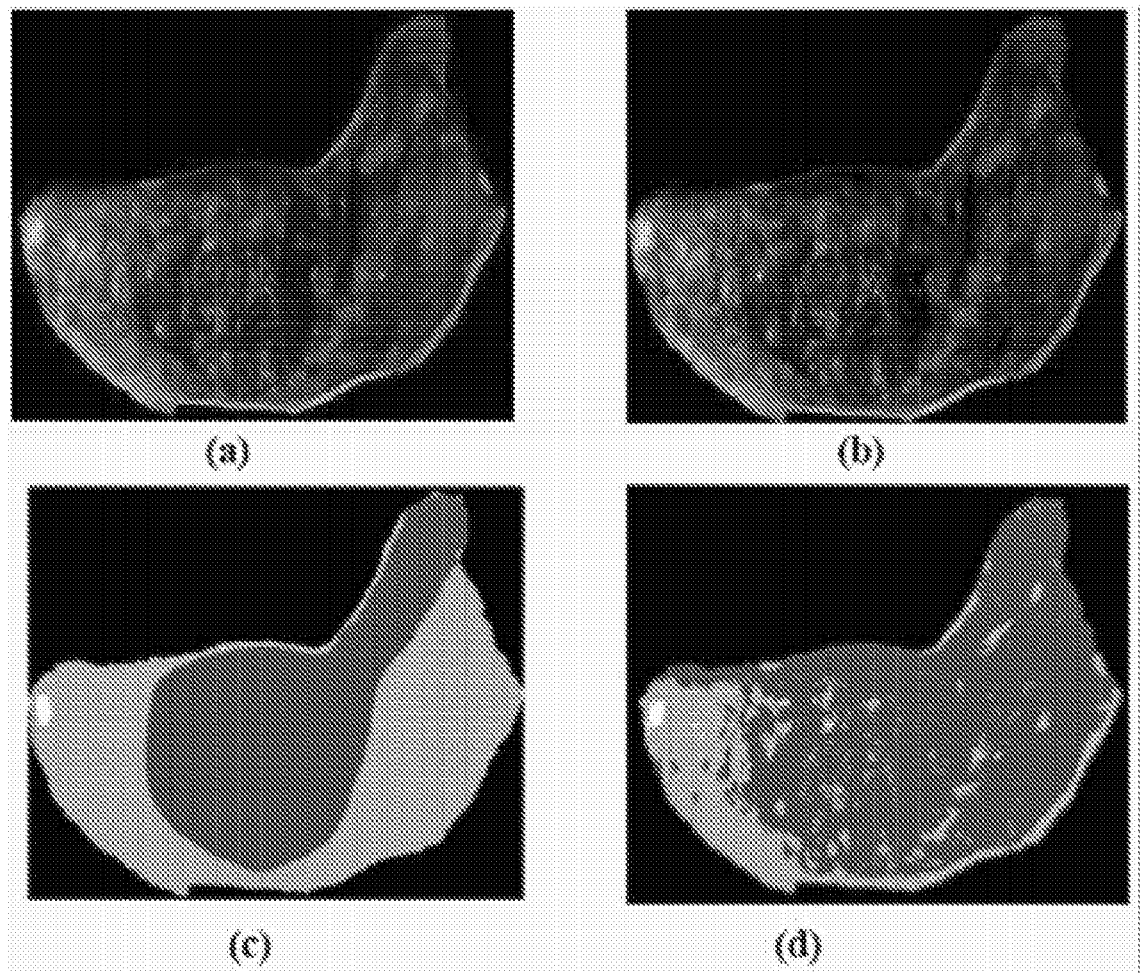
Figure 10:
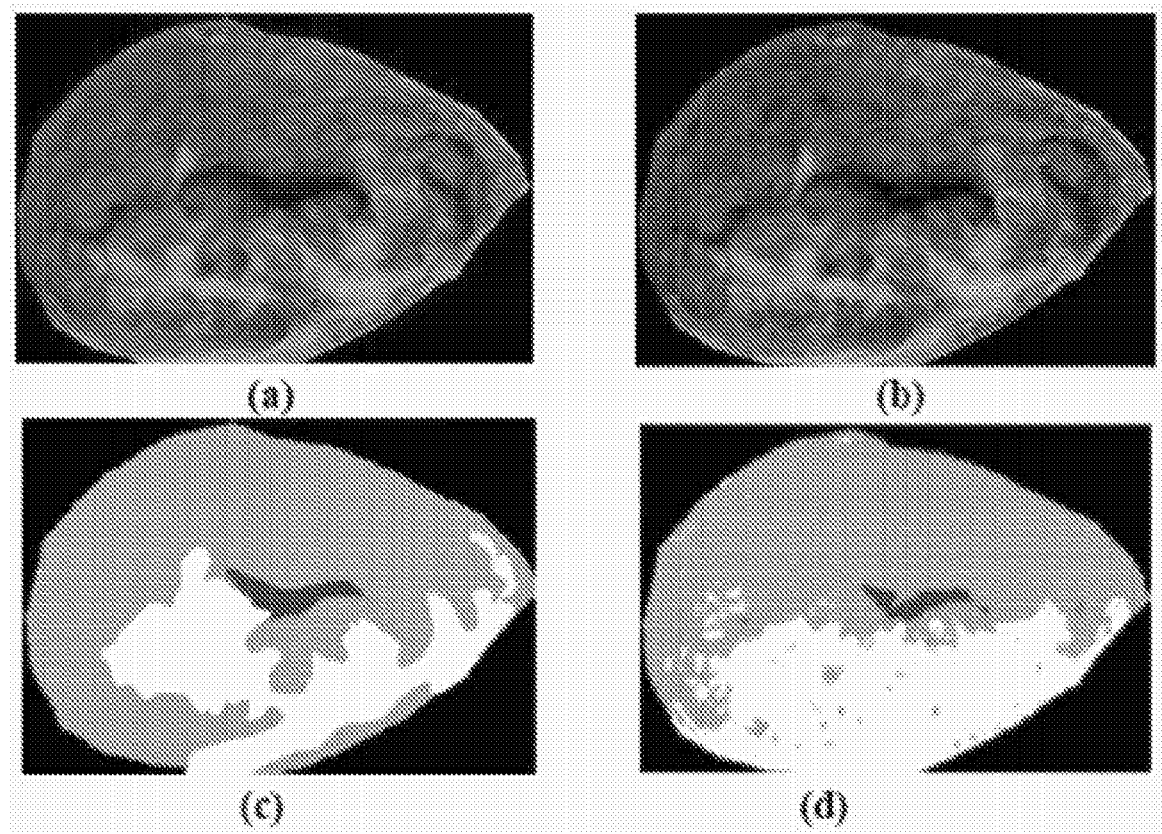
Figure 11:
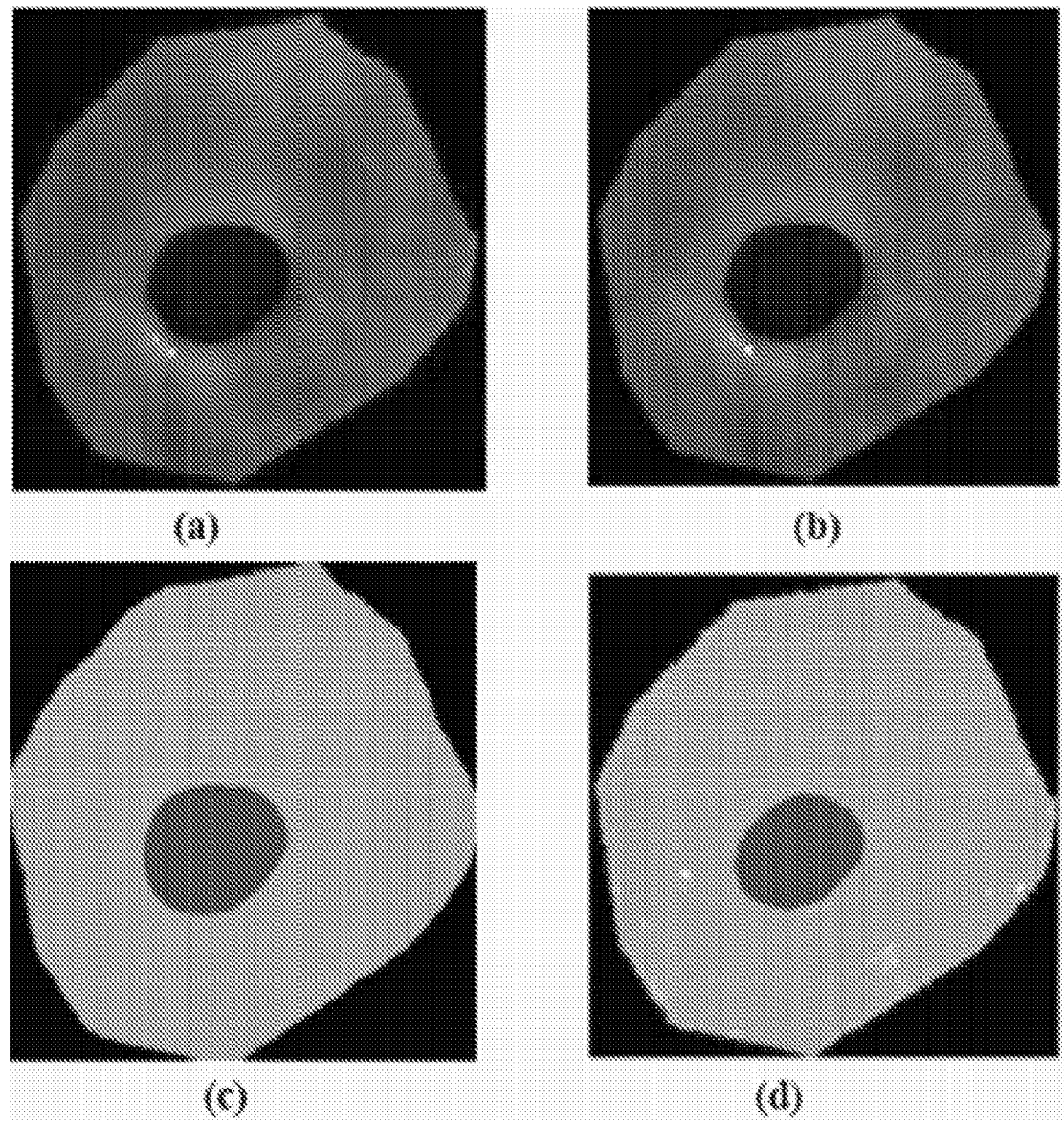

Then, as shown in FIG. 6, for each pixel p in the RGB ROI image $g_r$, the Euclidean distances $d_{p,i}$ between p and all training matrices $M_i$ are calculated. For each class i, the total number of the voxels N that are at distances lower than a predefined threshold T is calculated.

Finally, $P_{Color}$ is estimated using individual probabilities:

$$P_{p,i} = \frac{N_i}{\Sigma_{i \in \{r,b,w\}} N_i} \quad (6)$$

The final pixel-wise probability vector is constructed as $P = P_{Gray} \times P_{Color}$ and the initial tissue classification is obtained using the vector element with the highest probability.

D. GGMRF and the Final Segmentation

To accurately segment the ulcer region to the three classes, it is important to account for the low frequency intensity non-uniformity or inhomogeneity. For example, a 2D generalized Gauss-Markov random field (GGMRF) model [29] applied after the initial labeling of the ROI using a nonparametric approach proposed in [30] may be used. This step reduces noise effects and removes (smooths) inconsistencies of the initially segmented image by accounting for the 2D spatially homogeneous pair-wise interactions between the gray levels of the ROI image. Namely, the gray level values $q \in Q = \{0, \ldots, Q-1\}$ are considered as samples from a GGMRF model [29] represented for the 8-neighborhood of a voxel. The maximum aposteriori (MAP) estimates [29] and voxel-wise stochastic relaxation (iterative conditional mode (ICM) [31]) of q values of each wound image converted to a standard MRI format are employed as follows:

$$\tilde{q}_s = \arg\min[|q_s - \tilde{q}_s|^\alpha + \rho^\alpha \lambda^\beta \Sigma_{r \in v_s} \eta_{s,r} |q_s - \tilde{q}_s|^\beta] \quad (7)$$

Where q and $\tilde{q}_s$ are the original gray level values and the i expected estimates, respectively, at the observed 2D location, s=(x,y); $v_s$ is the 8-neighborhood system; $\eta_{s,r}$ is the GGMRF potential, and ρ and λ are scaling factors. The parameter β∈[1.03, 2.0] controls the level of smoothing (e.g., β=2 for smooth vs. β=1.01 for relatively abrupt edges). The parameter α∈{1,2} determines the Gaussian, α=2, or Laplace, α=1, prior distribution of the estimator.

Thus, these parameters determine the filtering geometry related to the output.

E. Examples

In the following examples, the training and testing images were acquired using regular digital camera with image resolution of 4000×3000 pixels. The total number of subjects is 11 patients. The ground truths are obtained by manual segmentation using a commercial image segmentation software and are verified by an expert.

To evaluate the results the percentage segmentation accuracy is calculated from the ground truth using Dice's coefficient (DC) [29] and the Hausdorff distance (HD) [30]. The DC measures the concordance between two enclosed volumes as follows:

$$DC \% = 100 \frac{2TP}{FP + 2TP + FN}$$

where FP represents the number of false positive (i.e. the total number of the misclassified pixels of the background), FN is the number of false negative (i.e. the total number of the misclassified pixel of the object), and TP is the true positive (i.e. total number of the correctly classified pixels).

On the other hand, the HD is defined as:

$$HD(X,Y) = \max\{\sup_{x \in X} \inf_{y \in Y} d(x,y), \sup_{y \in Y} \inf_{x \in X} d(x,y)\}$$

where X and Y are the boundaries of two different objects. It measures how far two subsets of a metric space are from each other. A high DC and a low HD are desirable for good segmentation.

In the Examples, all algorithms are run on a PC with 2.6 GHz Core i7 Quad processor, and 64 GB RAM. Algorithms are implemented using MATLAB® and C++.

The method was tested on 11 patients' datasets. The segmentation results of the exemplary method (A1) were compared with a comparison method (A2) based on Multiphase Chan-Vese level-sets models LSM described in [17], [32].

Table I summarizes the average segmentation accuracy (Dice's coefficient (DC) and the Hausdorff distance (HD), as well as the average execution time (in sec) for each method. The proposed method reaches 91.32% overall DC. It outperforms the LSM based method. For more meaningful comparison using HD, the average size of the ulcer ROI is 1024×1024 pixels. The exemplary method leads to superior results. It reaches 14.31 overall HD which reflects the accuracy of the proposed segmentation approach. The experimental results in Table I show that the performance of the exemplary method is superior in terms of accuracy over the LSM methods. This improvement in accuracy leads to more execution time. There is a tradeoff between the segmentation accuracy and execution time. The improvement of segmentation accuracy is more important than the execution time because it allows objective evaluation of the pressure ulcer (e.g., percentage of tissue types per classification) and better monitoring of the pressure ulcer over time by comparing current objective results with prior objective results.

TABLE I

AVERAGE DC (%) AND HD (MM) WITH STANDARD DEVIATION FOR SEGMENTATIONS OF OUR CLINICAL DATASETS USING DIFFERENT METHODS. THE AVERAGE EXECUTION TIME OF EACH METHOD IS SUMMARIZED IN THE LAST ROW.

| Method | A1 Exemplary Method | A2 (Chan-Vese LSM) |
|---|---|---|
| Dice's Coefficient (%) | 91.32 ± 4.53 | 68.72 ± 3.32 |
| Hausdorff Distance (Pixels) | 14.31 ± 2.34 | 54.47 ± 1.06 |
| Avg. Execution Time (Minutes) | 18.53 | 1.64 |

FIG. 6 through FIG. 11 show resulting images of different examples, including: (a) a colored ROI image, (b) a grayscale ROI image; (c) a segmented image resulting from the exemplary method, and (d) a resulting segmented image from the comparison method. Again, it is clear that the exemplary method outperforms LSM approach. It should be noted that, the LSM approach is using only the grayscale ROI images but the proposed method depends on both gray and colored ROI which makes it outperform the comparison method.

F. Conclusion

The system and method for automatic monitoring and evaluation of pressure ulcers according to the invention includes automated segmentation of tissue structures in pressure ulcer images using Linear Combinations of Discrete Gaussians to estimate the marginal distribution of the three main classes of the ROI gray image. The colored ROI image is used to calculate the three class probabilities of each pixel inside the ROI. The initial labeling is estimated based on the probabilities. In addition, to preserve continuity, the estimated labeled image is normalized and refined using a GGMRF image model. This method when tested, achieves a segmentation accuracy of 91.32% using Dice Similarity coefficient. This high accuracy allows the objective and computer implemented method to replace visual subjective assessment, thus achieving results not previously achievable. By implementing this approach on mobile devices, it can be used to provide guidance on medication and monitoring of patient response to treatment.

It will be understood that various details of the presently disclosed subject matter can be changed without departing from the scope of the subject matter disclosed and claimed herein.

Furthermore, the foregoing description is for the purpose of illustration only, and not for the purpose of limitation.

REFERENCES

Throughout this document, various references are cited. All such references are incorporated herein by reference, including the references set forth in the following list:

[1] J. F. Deprez, G. Cloutier and C. Schimitt, "3D Ultrasound Elastography for Early Detection of Lesions. Evaluation on a Pressure Ulcer Mimicking Phantom." in IEEE IMBC, Lyon, 2007.

[2] J. Larizgoitia Burgaña, Solución tecnológica para la parametrización objetiva de úlceras por presión basada en técnicas de procesado de imágenes., Bilbao: Universidad de Deusto, 2015.

[3] J. Leachtenauer, S. Kell, B. Turner, C. Newcomer, C. Lyder and M. Alwan, "A Non-Contact Imaging-Based Approach to Detecting Stage I Pressure Ulcers," New York, 2006.

[4] North York General Hospital, "Braden Scale for Predicting Pressure Sore Risk," NYGH, 2016.

[5] A. Prado, P. Andrades and S. Benitez, "Úlceras por presión," in Cirugia Plástica Esencial, Santiago de Chile, Universidad de Chile, pp. 106-118.

[6] R. Guadagnin, R. de S. Neves, L. Santana and D. Guilhem, "An image mining based approach to detect pressure ulcer stage," Pattern Recognition and Image Analysis, vol. 24, no. 2, pp. 292-296, 2014.

[7] http://www.ahrq.gov/professionals/systems/hospital/pressureulcertoolkit/putool1.html

[8] G. Bennett, C. Dealey and J. Posnett, "The cost of pressure ulcers in the UK." Age and Ageing, British Geriatrics Society, vol. 33, no. 3, pp. 230-235, 2004.

[9] J. J. Soldevilla-Agreda, J. E. Torra i Bou, J. Posnett and M. Mayan Santos, "The Burden of Pressure Ulcers in Spain." Wounds: a compendium of clinical research and practice, 2008.

[10] Tik Wai Poon, Marcia R. Friesesn, "Algorithms for Size and Color Detection of Smartphone Images of Chronic Wounds for Healthcare Applications", Digital Object Identifier 10.1109/ACCESS.2015.2487859, 2015.

[11] Sylvie Treuillet, Benjamin Albouy, and Yves Lucas. "Three-Dimensional Assessment of Skin Wounds Using a Standard Digital Camera", IEEE Transactions on Medical Imaging, vol. 28, no. 5, 2009.

[12] National Pressure Ulcer Advisory Panel, "Pressure Ulcer Scale for Healing (PUSH)," NPUAP, 1998.

[13] M. Kass, A. Witkin and D. Terzopoulos, "Snakes: Active Contour Models," International Journal of Computer Vision, pp. 321-331, 1988.

[14] S. Osher and R. Tsai, "Level Set Methods and Their Applications in Image Science," Communications in mathematical Sciences, vol. 1, no. 4, 509-573, 2003.

[15] J. A. Sethian, "Advancing Interfaces: Level Set and Fast Marching Methods," in Proceedings of the International Conference on Industrial and Applied Mathematics, 1999.

[16] S. Osher and R. P. Fedkiw, "Level Set Methods: An overview and Some Recent Results," Journal of Computational Physics, vol. 169, no. 2, pp. 463-502, 2001.

[17] T. F. Chan and L. A. Vese, "Active Contours Without Edges," IEEE Transactions on Image Processing, vol. 10, no. 2, pp. 266-277, 2001.

[18] J. Tang, "A color image segmentation algorithm based on region growing," in Computer Engineering and Technology (ICCET), 2010 2nd International Conference on (Volume:6), Chengdu, 2010.

[19] K. Zhang, W. Lu and P. Marziliano, "Automatic knee cartilage segmentation from multi-contrast MR images using support vector machine classification with spatial dependencies," Magnetic Resonance Imaging, pp. 1731-1743, 2013.

[20] H. Zhang, Q. Zhu and X.-f Guan, "Probe into Image Segmentation Based on Sobel Operator and Maximum Entropy Algorithm," in Computer Science & Service System (CSSS), Nanjing, 2012.

[21] H. Y. Yu, X. b. Zhi and J. I. Fan, "Image segmentation based on weak fuzzy partition entropy," Neurocomputing, pp. 994-1010, 2015.

[22] I. Esmail, N. J. Dabanloo and M. Vali, "Automatic classification of speech dysfluencies in continuous speech based on similarity measures and morphological image processing tools," Biomedical Signal Processing and Control, pp. 104-114, 2015.

[23] D. L. Wilson and J. A. Noble, "An adaptive segmentation algorithm for time-of-flight MRA data," IEEE Trans. Med. Imag., vol. 18, no. 10, pp. 938-945, October 1999.

[24] A. C. S. Chung and J. A. Noble, "Statistical 3D vessel segmentation using Rician distribution," in Proc. Int. Conf. Med. Image Comput. Comput.—Assist. Intervent., 1999, pp. 82-89.

[25] A. Webb, Statistical Pattern Recognition. New York: Wiley, 2002.

[26] A. Dufour, N. Passat, B. Naegel, and J. Baruthio, "Interactive 3D brain vessel segmentation from an example," in Proc. IEEE Int. Symp. Biomed. Imag., 2011, pp. 1121-1124.

[27] W. Liao, K. Rohr, C.-K. Kang, Z.-H. Cho, and S. Worz, "A generative MRF approach for automatic 3D segmentation of cerebral vasculature from 7 Tesla MRA images," in Proc. IEEE Int. Symp. Biomed. Imag., 2011, pp. 2041-2044.

[28] G. Gimel'farb, A. A. Farag, and A. El-Baz, "Expectation-maximization for a linear combination of Gaussians," in Proc. IEEE Int. Conf. Pattern Recognit., 2004, vol. 3, pp. 422-425.

[29] C. Bouman and K. Sauer, "A generalized gaussian image model for edgepreserving MAP estimation," IEEE Transactions on Image Processing, vol. 2, no. 3, pp. 296-310, 1993.

[30] N. J. Tustison, B. B. Avants, P. A. Cook, Y. Zheng, A. Egan, P. A. Yushkevich, and J. C. Gee, "N4ITK: improved N3 bias correction," IEEE Transactions on Medical Imaging, vol. 29, no. 6, pp. 1310-1320, 2010.

[31] J. Besag, "On the statistical analysis of dirty pictures," Journal of the Royal Statistical Society. Series B (Methodological), pp. 259-302, 1986.

[32] M. S. Aslan, E. Mostafa, H. Abdelmunim, A. Shalaby, and B. Arnold, A novel probabilistic simultaneous segmentation and registration using level set, Proceedings of the International Conference on Image Processing (ICIP), 2011.

[33] A. El-Baz, A. Elnakib, F. Khalifa, M. A. El-Ghar, P. McClure, A. Soliman, and G. Gimel'farb, "Precise segmentation of 3-D magnetic resonance angiography," IEEE Trans. Biomed. Eng., vol. 59, no. 7, pp. 2019-2029, 2012.

[34] Kanan C, Cottrell G W (2012) Color-to-Grayscale: Does the Method Matter in Image Recognition? PLoS ONE 7(1): e29740. doi:10.1371/journal.pone.0029740.

What is claimed is:

1. A method for evaluating a pressure ulcer, comprising:
a pre-processing step of detecting in a color input image a boundary of the pressure ulcer to get a RGB region of interest (ROI) image;
converting the RGB ROI image to a grayscale ROI image;
processing the grayscale ROI image using a Linear Combination of Discrete Gaussians (LCDG) process to estimate three main class probabilities of the grayscale ROI image;
processing the RGB ROI image using predetermined RGB values to estimate the three main class probabilities of the RGB ROI image;
combining the estimated three main class probabilities of the grayscale ROI image and the estimated three main class probabilities of the RGB ROI image to determine an estimated labeled image; and normalizing and refining the estimated labeled image using a Generalized Gauss-Markov Random Field (GGMRF) process to produce a final segmentation image.

2. The method of claim 1, wherein processing the grayscale ROI image using the LCDG process includes:
collecting a marginal empirical probability distribution Fs=(fs(q): q∈Q) of gray levels;
finding an initial LCDG-model that closely approximates Fs by using an initializing process to estimate numbers $C_p$-K, $C_n$, and parameters w, Θ (weights, means, and variances) of positive and negative Discrete Gaussians (DGs);
refining the initial LCDG-model with the numbers $C_p$ and $C_n$ by adjusting all other parameters with an expectation-maximization (EM) method to create a final LCDG-model;
splitting the final LCDG-model into K sub-models, one per each dominant mode, by minimizing expected errors of misclassification; and
selecting from the K sub-models a sub-model with a largest mean value as a desired model.

3. The method of claim 2, wherein the steps of finding the initial LCDG-model that closely approximates Fs and refining the initial LCDG-model produce a LCDG-model with nonnegative starting probabilities $p_{w,\Theta}(q)$, and the steps of splitting the final LCDG-model into K sub-models and selecting from the K sub-models a sub-model with the largest mean value increase a likelihood that the probabilities continue to be nonnegative, such upon completion of these steps, three probabilities for each pixel in the grayscale ROI image are obtained: $P_1$ which is the probability to be belonging to class 1, $P_2$ which is the probability to be belonging to class 2, and $P_3$ which is the probability to be belonging to class 3.

4. The method of claim 1, wherein processing the RGB ROI image using predetermined RGB values includes:
constructing a database for a set of labeled images for three main tissue classes;
constructing a matrix for each class by aggregating RGB values of all pixels of that class from training images which have been labeled;
for each pixel in the RGB ROI image, calculating Euclidean distances between the pixel and the matrix for each class;
determining for each of the three main tissue classes a total number of voxels that are at distances lower than a predefined threshold; and
estimating the three main class probabilities for each pixel in the RGB ROI image using individual probabilities.

5. The method of claim 1, wherein combining the estimated three main class probabilities of the grayscale ROI image and the estimated three main class probabilities of the RGB ROI image includes:
constructing a final pixel-wise probability vector as $P=P_{Gray} \times P_{Color}$; and
obtaining the estimated labeled image as an initial tissue classification of each pixel using a vector element with a highest probability.

6. A method of monitoring a pressure ulcer, comprising determining an objective change in the pressure ulcer by comparing current results with prior results of the method of evaluating the pressure ulcer of claim 1.

7. A system for monitoring and evaluating a pressure ulcer, comprising:
a microprocessor;
a data storage device in communication with the microprocessor;
an input/output device in communication with the microprocessor; and
a digital camera in communication with the microprocessor;
the microprocessor for executing instructions stored in the data storage device for:
receiving a color input image of the pressure ulcer from the digital camera;
detecting in the color input image a boundary of the pressure ulcer to get a RGB region of interest (ROI) image;
converting the RGB ROI image to a grayscale ROI image;
processing the grayscale ROI image using a Linear Combination of Discrete Gaussians (LCDG) process to estimate three main class probabilities of the grayscale ROI image;
processing the RGB ROI image using predetermined RGB values to estimate the three main class probabilities of the RGB ROI image;
combining the estimated three main class probabilities of the grayscale ROI image and the estimated three main class probabilities of the RGB ROI image to determine an estimated labeled image;
normalizing and refining the estimated labeled image using a Generalized Gauss-Markov Random Field (GGMRF) process to produce a final segmentation image; and
outputting the final segmentation image to the input/output device.

8. The system of claim 7, wherein processing the grayscale ROI image using the LCDG process includes:
collecting a marginal empirical probability distribution Fs=(fs(q): q∈Q) of gray levels;
finding an initial LCDG-model that closely approximates Fs by using an initializing process to estimate numbers $C_p$-K, $C_n$, and parameters w, Θ (weights, means, and variances) of positive and negative Discrete Gaussians (DGs);
refining the initial LCDG-model with the numbers $C_p$ and $C_n$ by adjusting all other parameters with an expectation-maximization (EM) method to create a final LCDG-model;
splitting the final LCDG-model into K sub-models, one per each dominant mode, by minimizing expected errors of misclassification; and
selecting from the K sub-models a sub-model with a largest mean value as a desired model.

9. The system of claim 8, wherein the steps of finding the initial LCDG-model that closely approximates Fs and refining the initial LCDG-model produces a LCDG-model with nonnegative starting probabilities $p_{w,\Theta}(q)$, and the steps of splitting the final LCDG-model into K sub-models and selecting from the K sub-models a sub-model with the largest mean value increases a likelihood that the probabilities continue to be nonnegative, such that upon completion of these steps, three probabilities for each pixel in the grayscale ROI image are obtained: $P_1$ which is the probability to be belonging to class 1, $P_2$ which is the probability to be belonging to class 2, and $P_3$ which is the probability to be belonging to class 3.

10. The system of claim 7, wherein processing the RGB ROI image using predetermined RGB values includes:
   constructing a database for a set of manually labeled images for three main tissue classes;
   constructing a matrix for each class by aggregating RGB values of all pixels of that class from training images which have been manually labeled by an expert;
   for each pixel in the RGB ROI image, calculating Euclidean distances between the pixel and the matrix for each class;
   determining for each of the three main tissue classes a total number of voxels that are at distances lower than a predefined threshold; and
   estimating the three main class probabilities for each pixel in the RGB ROI image using individual probabilities.

11. The system of claim 7, wherein combining the estimated three main class probabilities of the grayscale ROI image and the estimated three main class probabilities of the RGB ROI image includes:
   constructing a final pixel-wise probability vector as $P=P_{Gray} \times P_{Color}$; and
   obtaining the estimated labeled image as an initial tissue classification of each pixel using a vector element with a highest probability.

12. The system of claim 7, further comprising a power supply in communication with the microprocessor, the data storage device, the input/output device, and the digital camera; wherein the integrated power supply, the microprocessor, the data storage device, the input/output device, and the digital camera are integrated into a unitary device that can be carried by a caregiver and utilized at a bedside of a patient.

* * * * *